United States Patent
Shiba et al.

(10) Patent No.: US 8,992,894 B2
(45) Date of Patent: Mar. 31, 2015

(54) ORAL STAIN REMOVER AND ORAL COMPOSITION

(75) Inventors: Toshikazu Shiba, Okaya (JP); Atsushi Saitou, Okaya (JP); Kazuyoshi Okada, Osaka (JP); Yoshio Tsujino, Osaka (JP)

(73) Assignees: Mandom Corporation, Osaka (JP); REGENETISS Inc., Nagano (JP)

( * ) Notice: Subject to any disclaimer, the term of this patent is extended or adjusted under 35 U.S.C. 154(b) by 106 days.

(21) Appl. No.: 12/304,965

(22) PCT Filed: Jun. 14, 2007

(86) PCT No.: PCT/JP2007/062029
§ 371 (c)(1),
(2), (4) Date: Dec. 15, 2008

(87) PCT Pub. No.: WO2007/145287
PCT Pub. Date: Dec. 21, 2007

(65) Prior Publication Data
US 2009/0280072 A1 Nov. 12, 2009

(30) Foreign Application Priority Data
Jun. 16, 2006 (JP) ................................. 2006-166767

(51) Int. Cl.
*A61Q 11/00* (2006.01)
*A61K 8/24* (2006.01)
*A61K 8/55* (2006.01)
*A61Q 11/02* (2006.01)

(52) U.S. Cl.
CPC . *A61Q 11/00* (2013.01); *A61K 8/24* (2013.01); *A61K 8/55* (2013.01); *A61Q 11/02* (2013.01)
USPC ................. 424/57; 424/49; 433/216

(58) Field of Classification Search
USPC ....................... 424/49, 57; 433/216
See application file for complete search history.

(56) References Cited

U.S. PATENT DOCUMENTS

| | | | |
|---|---|---|---|
| 5,939,052 A * | 8/1999 | White et al. | 424/52 |
| 6,183,515 B1 * | 2/2001 | Barlow et al. | 623/16.11 |
| 7,192,571 B2 * | 3/2007 | Ahn et al. | 424/49 |
| 2002/0160910 A1 * | 10/2002 | Sanbayashi et al. | 502/208 |
| 2003/0133884 A1 | 7/2003 | Chang et al. | |
| 2004/0033204 A1 * | 2/2004 | Ahn et al. | 424/49 |

FOREIGN PATENT DOCUMENTS

| | | |
|---|---|---|
| JP | 58-121204 A | 7/1983 |
| JP | 63-30408 A | 2/1988 |
| JP | 1-213222 A | 8/1989 |
| JP | 9-175966 A | 7/1997 |
| JP | 10-182386 A | 7/1998 |
| JP | 2002-306126 A | 10/2002 |
| JP | 2003-2815 A | 1/2003 |
| JP | 2003-212743 A | 7/2003 |
| JP | 2003-526648 A | 9/2003 |
| JP | 2005-80617 A | 3/2005 |
| WO | WO-02/45677 A1 | 6/2002 |
| WO | WO-2006/106947 A1 | 10/2006 |

OTHER PUBLICATIONS

"Function of tooth brushing," Summery of Tooth Brushing Technical Characteristics, 1984, pp. 117.

* cited by examiner

*Primary Examiner* — Lezah Roberts
(74) *Attorney, Agent, or Firm* — Birch, Stewart, Kolasch & Birch, LLP

(57) ABSTRACT

An oral stain remover which can remove a stain or a dental plaque effectively without a need of brushing the surface of teeth with a toothbrush or the like, and an oral composition containing the stain remover. An oral stain remover contains a salt of ultraphosphoric acid, and an oral composition contains the oral stain remover.

2 Claims, 1 Drawing Sheet

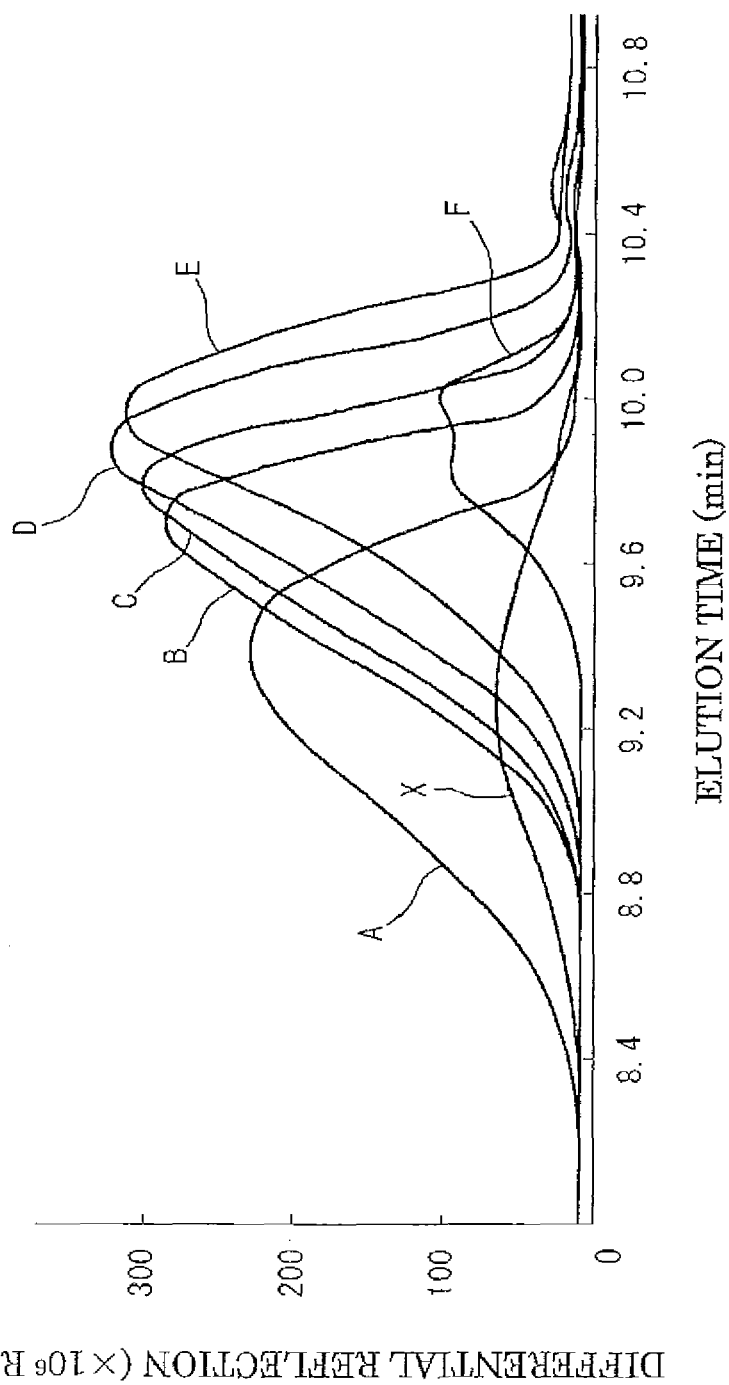

ORAL STAIN REMOVER AND ORAL COMPOSITION

TECHNICAL FIELD

The present invention relates to an oral stain remover and an oral composition. More specifically, the present invention relates to an oral stain remover which prevents stain caused by plaque, foods, tea, coffee, cigarettes or the like from being deposited on the surface of teeth and also can remove deposited stain effectively, and an oral composition containing the stain remover.

BACKGROUND ART

Conventionally, some attempts to add a salt of polyphosphoric acid or a salt of metaphosphoric acid to an oral composition such as dentifrice have been made in order to remove stain or plaque adhered to the surface of teeth. For example, there have been reported an oral composition in which a salt of polyphosphoric acid or a salt of metaphosphoric acid is used together with menthol or anethole (refer to Patent Document 1), an oral composition in which a water-soluble salt of pyrophosphoric acid is used together with a salt of polyphosphoric acid (refer to Patent Document 2), and a tooth cleaning material in which a salt of polyphosphoric acid is used together with a natural scrubbing agent (refer to Patent Document 3).

However, these oral compositions and tooth cleaning materials have some disadvantages such that stain and plaque adhered to the surface of teeth cannot be completely removed from the teeth with a toothbrush or the like, and stain or plaque builds up in spite of daily brushing of the teeth. Such oral compositions and tooth cleaning materials also have another disadvantage such that there can be hardly removed from teeth stain and plaque adhered to the teeth where a toothbrush is difficulty reached.

Accordingly, there has been desired to develop a stain remover which can effectively remove stain and plaque from teeth without the need of brushing the surface of teeth with a toothbrush or the like and also prevents stain and the like from being deposited on the surface of teeth from which once stain and plaque have been removed.

Meanwhile, ultraphosphoric acid has been known to have antibacterial properties, and conventionally has been used as a food preservative (refer to Patent Documents 4 and 5). It has also been reported that the ultraphosphoric acid exhibits an effect of inhibiting change in color of a composition containing tannin (refer to Patent Document 6). However, it has not yet been reported that the ultraphosphoric acid shows a function for removing stain.

Patent Document 1: Japanese Unexamined Patent Publication No. Sho 63-30408
Patent Document 2: Japanese Unexamined Patent Publication No. Hei 8-175966
Patent Document 3: Japanese Unexamined Patent Publication No. Hei 10-182386
Patent Document 4: Japanese Unexamined Patent Publication No. Sho 58-121204
Patent Document 5: Japanese Unexamined Patent Publication No. 2005-80617
Patent Document 6: Japanese Unexamined Patent Publication No. 2002-306126

DISCLOSURE OF INVENTION

Problem to be Solved by the Invention

An object of the present invention is to provide an oral stain remover which can effectively remove stain and plaque from teeth without the need of brushing the surface of teeth with a toothbrush or the like, and also prevents stain or plaque from being deposited on the surface of teeth from which once stain or plaque has been removed, and an oral composition containing the stain remover.

Means for Solving the Problem

The present invention relates to:

[1] an oral stain remover containing a salt of ultraphosphoric acid;
[2] the oral stain remover according to the above-mentioned [1], wherein the average degree of polymerization of the salt of ultraphosphoric acid is 7 to 12;
[3] an oral composition containing the stain remover according to above-mentioned [1] or [2];
[4] the oral composition according to the above-mentioned [3], wherein pH of the oral composition is 4 to 8; and
[5] the oral composition according to above-mentioned [3] or [4], wherein the content of the salt of ultraphosphoric acid in the oral composition is 0.5 to 10% by weight.

Advantage of the Invention

An oral stain remover and an oral composition containing the stain remover of the present invention can effectively remove stain and plaque without the need of brushing the surface of teeth with a toothbrush or the Like, and also prevents stain or the like from being deposited on the surface of teeth from which once stain or plaque has been removed.

When a salt of ultraphosphoric acid having an average degree of polymerization of 7 to 12 is used in the oral stain remover of the present invention, removal effect of stain and plaque can be further enhanced.

BRIEF DESCRIPTION OF THE DRAWINGS

FIG. 1 is a gel permeation chromatogram of a salt of ultraphosphoric acid and fractions A to F obtained in Examples 15 to 21 of the present invention.

BEST MODE FOR CARRYING OUT THE INVENTION

The stain remover of the present invention contains a salt of ultraphosphoric acid. The salt of ultraphosphoric acid is one of condensed phosphate salts, i.e. salts of phosphoric acid, which are prepared by polymerizing a salt of ultraphosphoric acid so that two or more $PO_4$ tetrahydras of the salt of ultraphosphoric acid possess oxygen atom of other $PO_4$ tetrahydras of the salt of ultraphosphoric acid.

The condensed phosphate salt is classified into a salt of polyphosphoric acid, a salt of metaphosphoric acid, and a salt of ultraphosphoric acid, in accordance with the molar ratio of $M_2O/P_2O_5$ wherein M is a monovalent metal represented by an alkali metal.

The salt of polyphosphoric acid is a linear compound represented by the formula (I):

wherein M is the same as defined above, and m is an integer of not less than 2, which has a molar ratio (R) of $M_2O/P_2O_5$ satisfying $2 \geq R > 1$ wherein M is the same as defined above.

The salt of metaphosphoric acid is a cyclic or linear extremely long chain compound represented by the formula (II):

wherein M is the same as defined above, n is an integer of not less than 3, which has a molar ratio (R) of $M_2O/P_2O_5$ satisfying 1, wherein M is the same as defined above. Both of the above-mentioned salt of polyphosphoric acid and the above-mentioned salt of metaphosphoric acid are sometimes referred to as a salt of polyphosphoric acid, respectively.

The salt of ultraphosphoric acid is a compound represented by the formula (III):

[Chemical Formula 1]

$$\frac{x}{2}M_2O \cdot \frac{y}{2}P_2O_5 \quad (III)$$

wherein M is the same as defined above, and each of x and y is a positive integer respectively and satisfies 0<x/y<1, which has a molar ratio (R) of $M_2O/P_2O_5$ satisfying 1>R>0 in which M is the same as defined above. The compound has a crosslinked structure including a branched $PO_4$ group in its molecule, and a unique structure as compared with a salt of polyphosphoric acid and a salt of metaphosphoric acid. In Formula (II), x is preferably an integer of 2 to 20, and y is preferably an integer of 4 to 20. Each of x and y is preferably an integer which satisfies an average degree of polymerization of 7 to 12, respectively, from the viewpoint of enhancing the removal effect of stain.

Examples of the salt of ultraphosphoric acid include alkali metal salts such as sodium salt and potassium salt, and ammonium salts. Among them, a sodium salt is preferable.

The salt of ultraphosphoric acid exhibits excellent removal effect of stain even when the salt of ultraphosphoric acid is used as it is. The average degree of polymerization of the salt of ultraphosphoric acid is preferably 7 to 12, more preferably 8.5 to 115, and even more preferably 9 to 11 from the viewpoint of more enhancing the removal effect of stain or plaque.

A method for fractionating a salt of ultraphosphoric acid having a specific average degree of polymerization is not particularly limited. As the method, there can be cited, for instance, a method which employs the difference of the salts of ultraphosphoric acid in solubility in an alcohol-aqueous solvent. The salt of ultraphosphoric acid has such a property that the higher the polymerization degree (molecular weight) becomes, the lower the solubility to an alcohol-aqueous solvent becomes, and that the higher the alcohol concentration becomes, the lower the solubility to an alcohol-aqueous solvent becomes. By employing this property, the salts of ultraphosphoric acid can be easily fractionated so as to have a fixed average degree of polymerization.

Examples of the alcohol used in fractionation include methanol, ethanol, isopropanol, n-propanol, t-butanol, and the like. Among them, ethanol is preferable in consideration of a solvent remaining after fractionation.

As a method for fractionating, there can be cited, for instance, the following operation: First, the salt of ultraphosphoric acid is dissolved in water in a ratio so that the amount of water is 300 to 500 parts by weight based on 100 parts by weight of the salt of ultraphosphoric acid, to prepare an aqueous solution of a salt of ultraphosphoric acid. The above-mentioned water is not particularly limited and is preferably purified water.

Incidentally, it is preferable to add acid or alkali to the aqueous solution of the salt of ultraphosphoric acid so as to make the solution neutral or weak acid from the viewpoint of preventing the decomposition of the salt of ultraphosphoric acid. More specifically, it is desired that pH of the aqueous solution of the salt of ultraphosphoric acid is adjusted to preferably 4 to 7, more preferably 5 to 7.

Next, an alcohol is added to the aqueous solution of the salt of ultraphosphoric acid in a ratio so that the amount of alcohol is 10 to 20 parts by weight based on 100 parts by weight of the salt of ultraphosphoric acid, followed by stirring. At this stage, since an alcohol is difficultly dissolved in the aqueous solution of the salt of ultraphosphoric acid in a high concentration, the solution separates into the aqueous solution of the salt of ultraphosphoric acid as a lower layer and the aqueous alcohol solution of the salt of ultraphosphoric acid as an upper layer from each other.

When an alcohol is contained in the aqueous solution of a salt of ultraphosphoric acid, the solubility of the salt of ultraphosphoric acid lowers as its polymerization degree increases. Therefore, the salt of ultraphosphoric acid having a higher polymerization degree is dissolved in the aqueous solution of the salt of ultraphosphoric acid in the lower layer, while the salt of ultraphosphoric acid having a lower polymerization degree is dissolved in the aqueous alcohol solution of the salt of ultraphosphoric acid of the upper layer.

When the upper layer is separated from the lower layer, it is preferable that the upper layer is separated from the lower layer by using, for instance, a centrifugal separator from the viewpoint of facilitating separation of the upper layer from the lower layer.

To the separated aqueous alcohol solution of the upper layer, an alcohol is added so that the amount of the alcohol is 10 to 20 parts by weight based on 100 parts by weight of the salt of ultraphosphoric acid, followed by stirring. Thus, the concentration of the alcohol in the aqueous alcohol solution increases. As a result, the solution separates into an aqueous solution of the salt of ultraphosphoric acid having a high polymerization degree as a lower layer and an aqueous alcohol solution of the salt of ultraphosphoric acid having a lower polymerization degree as an upper layer from each other, as in the above.

Repeating a separation operation in desired times; a salt of ultraphosphoric acid having a fixed average degree of polymerization can be easily obtained. For instance, when a salt of ultraphosphoric acid having an average degree of polymerization of 7 to 12 is prepared, the separation operation can be repeated 3 to 5 times by using an alcohol-aqueous solvent. Incidentally, when the salt of ultraphosphoric acid is isolated, an objective fraction may be freeze-dried or condensed under reduced pressure.

The content of the salt of ultraphosphoric acid in an oral stain remover of the present invention is not particularly limited. The oral stain remover may be constituted only with the salt of ultraphosphoric acid, or may contain other components within the scope of not impairing the object of the present invention. Examples of the other components include lubricants, solvents, flavoring agents, binders, foaming agents, coloring agents, preservatives, and the like.

The oral composition of the present invention contains the above-mentioned oral stain remover. The content of the stain remover in the oral composition is not particularly limited. The oral composition may be constituted with only the stain remover, or may contain other components within the scope of not impairing the object of the present invention. Examples of the other components include solvents such as ethanol; solubilizers such as polyoxyethylene hydrogenated castor oil and polyoxyethylene polyoxypropylene glycol; lubricants such as glycerin and sorbitol; flavors such as saccharine sodium, peppermint oil and menthol; binders such as carrageenan and carboxymethylcellulose sodium; foaming agents such as sodium lauryl sulfate; abrasives such as calcium carbonate, and silicic anhydride; coloring agents such as caramel and a legal coloring matter; preservatives such as paraben and sodium benzoate; pH adjusters such as phosphate salts and citrate salts; water; and the like. However, the present invention is not limited to those exemplified ones.

The content of the salt of ultraphosphoric acid in the oral composition is preferably at least 0.5% by weight, more preferably at lest 1% by weight from the viewpoint of efficiently exhibiting the removal effect of stain and plaque. When the content of the salt of ultraphosphoric acid in the oral composition is so much, the improvement in removal effect of stain and plaque cannot be expected, and there is a tendency that economic efficiency is lowered. Accordingly, the content of the a salt of ultraphosphoric acid in the oral composition is preferably at most 10% by weight, more preferably at most 3% by weight. From these perspectives, the content of the salt of ultraphosphoric acid in the oral composition is preferably 0.5 to 10% by weight, more preferably 1 to 5% by weight.

The pH of the oral composition is preferably at most 8, more preferably at most 6.5 from the viewpoint of efficiently exhibiting the removal effect of stain and plaque, and preferably at least 4, more preferably at least 5 from the viewpoint of protecting the tooth enamel from caries. From these perspectives, the pH of the oral composition is preferably 4 to 8, more preferably 5 to 6.5.

The oral composition of the present invention can be used for abrasives for teeth, mouth rinses, denture cleansers, tooth patches, and the like. Also, since the oral composition of the present invention contains a stain remover which is excellent in removal effect of stain and plaque, the oral composition can be effectively used as an oral composition for not only humans but also pets those not brushing their teeth.

EXAMPLES

Next, the present invention will be illustrated specifically with reference to working examples, but is not limited to those examples.

Example 1 and Comparative Examples 1 and 2

Stain Removal Test

As test solutions, 100 mM (concentration of phosphoric acid) of sodium ultraphosphate aqueous solution (pH 6.2), 100 mM (concentration of phosphoric acid) of sodium metaphosphate aqueous solution (pH 6.2), and 100 mM (concentration of phosphoric acid) of sodium phosphate aqueous solution (pH 6.2) were prepared, respectively. More specifically, sodium ultraphosphate [manufactured by TAIHEI CHEMICAL INDUSTRIAL CO., LTD, food additive standard], sodium metaphosphate [manufactured by TAIHET CHEMICAL INDUSTRIAL CO., LTD, food additive standard], and monosodium phosphate ($NaH_2PO_4.2H_2O$) were dissolved in 80 mL of purified water, respectively in a desired amount to give a solution having a phosphoric acid concentration of 100 mM, and pH of each solution was adjusted to 6.2 by using 5N NaOH or 5N HCl. Thereafter, purified water was added to each of the solutions so that the total amount was 100 mL.

Aside from this, 4 g of tea leaves were immersed in 200 mL of boiled purified water for 10 minutes, and this liquid was filtered through a filter paper (No. 5B, manufactured by WHATMAN INTERNATIONAL LTD.) to obtain a tea extract.

Next, 150 mg of hydroxyapatite powder was put into a 15 mL centrifuge tube, and 10 mL of purified water was added thereto. The centrifuge tube was tipped over for mixing the hydroxyapatite powder with water to prepare a mixed solution. This mixed solution was separated by means of a centrifugal separator [5200 type, manufactured by Kubota Corporation] (1,500 g, 2 minutes) to remove a supernatant. To the mixed solution from which the supernatant was removed was added 5 mL of the tea extract, and the centrifuge tube was tipped over for mixing the mixed solution with the tea extract. Thereafter, the resulting solution was separated by centrifugation (1500 g, 2 minutes), and the supernatant was removed again from the mixture.

In order to wash tea stain which was not adsorbed to the hydroxyapatite powder included in the mixed solution from which supernatant had been removed, 10 mL of purified water was added to the mixed solution, and the centrifuge tube was tipped over for mixing the mixed solution with water for 1 minute. Thereafter, the supernatant was separated by centrifugation (1500 g, 2 minutes). After repeating this operation once more, 10 mL of purified water or 10 mL of each test solution was added to the mixed solution, the centrifuge tube was tipped over for mixing them for 1 minute, and the mixed solution was separated by centrifugation (1,500 g, 2 minutes). After the supernatant was removed from the mixed solution, 10 mL of purified water was added to the mixed solution, and the centrifuge tube was tipped over for mixing them for 1 minute. Thereafter, the supernatant was separated by centrifugation (1,500 g, 2 minutes).

After removing the supernatant from this mixed solution, 13 mL of purified water was added to the mixed solution, the centrifuge tube was tipped over for mixing them for 1 minute, and the mixed solution was filtered through a filter pad [Cat. No. AP10, manufactured by Millipore Corp.], thereby subjecting to suction filtration. The resulting product was air dried, and scanned by means of an image scanner [GT-8300UF, manufactured by SEIKO EPSON CORPORATION]. Then, the image was inverted to be negative, and analyzed with an image analysis program Image J [internet] [URL:].

The residual ratio of the tea stain in each test solution was evaluated as 100% when treated in the same manner as in the above except that purified water was used in place of the test solution. The residual ratio of the tea stain in each test solution was evaluated as a background (residual ratio: 0%) when treated in the same manner as in the above except that the tea extract was not added to the solution. The residual ratio of the tea stain in each test solution was calculated. This test was repeated three times, and its average was employed. The results are shown in Table 1.

TABLE 1

| | | Residual Ratio of Stein (%) | | | |
|---|---|---|---|---|---|
| | | 1st | 2nd | 3rd | Average |
| Example 1 | Sodium Ultraphosphate | 5.51 | 8.41 | 6.02 | 6.64 |
| Comp. Ex 1 | Sodium Metaphosphate | 32.13 | 39.02 | 33.23 | 34.79 |
| Comp. Ex 2 | Sodium Phosphate | 87.36 | 96.94 | 87.23 | 90.51 |

From the results shown in Table 1, when a salt of ultraphosphoric acid is used (Example 1), it can be seen that the removal effect of stain is remarkably higher as compared with the case where a salt of metaphosphoric acid (Comparative Example 1) or a salt of phosphoric acid (Comparative Example 2) is used.

Examples 2 to 5 pH Influence Test

In 80 mL of purified water, 1 g of sodium a salt of ultraphosphoric acid [manufactured by MTTEJTMA CHEMICAL Co., LTD., food additive standard] was dissolved, and its pH was adjusted to 5.5, 6.2, 6.9 or 7.6 with a 5N NaOH aqueous solution. Thereafter, purified water was added to the solution so that the total amount of the solution was 100 mL (100 mM as a concentration of phosphoric acid). These solutions were used as test solutions, and a stain removal tests was carried out in the same manner as in Example 1. The results are shown in Table 2.

TABLE 2

|  |  | Residual Ratio of Stain (%) | | | |
| --- | --- | --- | --- | --- | --- |
|  |  | 1st | 2nd | 3rd | Average |
| Example 2 | pH 5.5 | 10.26 | 8.60 | 9.50 | 9.45 |
| Example 3 | pH 6.2 | 8.87 | 8.94 | 10.60 | 9.47 |
| Example 4 | pH 6.9 | 16.02 | 14.01 | 15.63 | 15.22 |
| Example 5 | pH 7.6 | 25.43 | 24.38 | 23.62 | 24.48 |

From the results shown in Table 2, it can be seen that the removal effect of stain and plaque is lowered in accordance with the increase of pH value, and that the lower the pH value of the test solutions is, the removal effect of stain and plaque becomes more excellent. In addition, it can be seen that the removal effect of stain and plaque at pH 5.5 (Example 2) is almost the same as that at pH 6.2 (Example 3), and that the removal effect of stain and plaque in these cases is about 2.5 times greater than that of the case where the pH was 7.6 which means weak alkali (Example 5).

Examples 6 to 14

Concentration Dependency Test

Each aqueous solution (pH 6.2) having a sodium ultraphosphate [manufactured by MITEJIMA CHEMICAL Co., LTD., food additive standard] content of 0, 0.1, 0.2, 0.4, 0.6, 0.8, 1.0, 3.0, 5.0 or 10.0 w/v % was prepared to give a test solution. Using these test solutions, stain removal test was carried out in the same manner as in Example 1. The results are shown in Table 3 together with the results of Comparative Example 2.

TABLE 3

|  | Concentration (w/v %) | Residual Ratio of Stain (%) |
| --- | --- | --- |
| Comparative Example 2 | 0 | 100.00 |
| Example 6 | 0.1 | 79.65 |
| Example 7 | 0.2 | 61.48 |
| Example 8 | 0.4 | 31.28 |
| Example 9 | 0.6 | 19.10 |
| Example 10 | 0.8 | 15.39 |
| Example 11 | 1.0 | 11.88 |
| Example 12 | 3.0 | 2.70 |
| Example 13 | 5.0 | 1.88 |
| Example 14 | 10.0 | 1.04 |

From the results shown in Table 3, when the concentration of the salt of ultraphosphoric acid is not more than 0.4 w/v %, it can be seen that the removal effect of stain greatly depends on the concentration. On the other hand, when the concentration of the salt of ultraphosphoric acid is not less than 1 w/v %, it can be seen that the dependency of the removal effect of stain on the concentration is lowered in accordance with the increase of the concentration of the salt of ultraphosphoric acid.

Examples 15 to 21

Fractionation Test of a Salt of Ultraphosphoric Acid (1)

To 80 g of sodium ultraphosphate [manufactured by MITEJIMA CHEMICAL Co., LTD., food additive standard], 254 mL of purified water and 50 mL of ION NaOH aqueous solution were added, and the sodium ultraphosphate was dissolved in the NaOH aqueous solution, to prepare an ultraphosphoric acid aqueous solution (pH 6.0). Ethanol in an amount of 15 mL was added to this ultraphosphoric acid aqueous solution and stirred. The resulting mixture was allowed to stand still at room temperature for 10 minutes, and centrifuged (10,000 g, 10 minutes) by means of a centrifugal separator [5200 type, manufactured by Kubota Corporation] to separate an upper layer 1a from a lower layer 1b. The obtained lower layer 1b was given as fraction A.

Ethanol in an amount of 16 mL was added to the upper layer 1a and mixed with each other. The resulting mixture was allowed to stand still at room temperature for 10 minutes, and centrifuged (10,000 g, 10 minutes), to separate an upper layer 2a from a lower layer 2b. The obtained lower layer 2b was given as fraction B.

Ethanol in an amount of 17 mL was added to the upper layer 2a and stirred them. The resulting mixture was allowed to stand still at room temperature for 10 minutes, and centrifuged in the same manner as in the above, to separate an upper layer 3a from a lower layer 3b. The obtained lower layer 3b was given as fraction C.

Ethanol in an amount of 17.5 mL was added to the upper layer 3a and stirred them. The resulting mixture was allowed to stand still at room temperature for 10 minutes, and centrifuged in the same manner as in the above, to separate an upper layer 4a from a lower layer 4b. The obtained lower layer 4b was given as fraction D.

Ethanol in an amount of 18.5 mL was added to the upper layer 4a and stirred them. The resulting mixture was allowed to stand still at room temperature for 10 minutes, and centrifuged in the same manner as in the above, to separate an upper layer 5a from a lower layer 5b. The obtained lower layer 5b was given as fraction E, and the upper layer 6a was given as fraction F.

Each fraction thus obtained was analyzed by gel permeation chromatography under the following conditions. The results are shown in FIG. 1. From the results shown in FIG. 1, it can be seen that fraction A (A in FIG. 1) had the highest average molecular weight (average degree of polymerization), that the average molecular weight (average degree of polymerization) was decreased in the order of fraction B (B in FIG. 1), fraction C (C in FIG. 1), fraction D (D in FIG. 1) and fraction E (E in FIG. 1), and that fraction F (F in FIG. 1) had the lowest average molecular weight (average degree of polymerization). From this fact, it can be seen that a salt of ultraphosphoric acid having a specific average molecular weight (average degree of polymerization) can be easily obtained by employing the difference in solubility with an alcohol-aqueous solvent. Incidentally, the shorter the dissolving time is, the higher the molecular weight (polymerization degree) is. The symbol X in FIG. 1 denotes the data when sodium ultraphosphate before fractionating was used.

<High-Performance Liquid Chromatography (HPLC) Conditions>

Analytical instrument: Shimadzu Corporation, trade name: Shimadzu LC2010C HPLC

Column; Showa Denko K. K., trade name: Sodex OHpak SB-803HQ

Column temperature: 30° C.

Solvent: 0.1 M NaCl

Flow rate: 1 mL/min

Detector: Shimadzu Corporation, trade name: Differential refractometer, detector RID-10A Next, sodium ultraphosphate and each of fractions A to F obtained above were dissolved in or diluted with purified water so as to have a concentration of 100 mM as a concentration of phosphoric acid, and the pH was adjusted to 6.2 by using 5N NaOH aqueous solution or 5N aqueous HCl. These were used as test solutions, and stain removal tests were carried out in the same manner as in Example 1. The results are shown in Table 4.

TABLE 4

|  |  | Residual Ratio of Stain (%) |
|---|---|---|
| Example 15 | Sodium Ultraphosphate | 10.18 |
| Example 16 | Fraction A | 14.77 |
| Example 17 | Fraction B | 12.57 |
| Example 18 | Fraction C | 7.74 |
| Example 19 | Fraction D | 5.03 |
| Example 20 | Fraction E | 7.63 |
| Example 21 | Fraction F | 12.62 |

From the results shown in Table 4, it can be seen that each of the fractions C to E is more excellent in removal effect of stain and plaque than the salt of ultraphosphoric acid before fractionating. Also, it can be seen that the fraction D is most excellent in removal effect of stain and plaque among them, and that the removal effect of stain and plaque of the fraction D is about 2 times that of the salt of ultraphosphoric acid before fractionating.

Fractionation Test of a Salt of Ultraphosphoric Acid
(2)

Electrophoresis of the fractions A to F obtained above and the sodium ultraphosphate before fractionating was carried out. Each average degree of polymerization (average chain length) of the fractions and the sodium ultraphosphate before fractionating was determined by their mobility. More specifically, the electrophoresis was carried out by using 15% polyacrylamide gel [acrylamide:bisacrylamide (weight ratio)=30: 0.8] under the conditions of a specimen concentration of 1% by weight, an applied amount of 4 μL and a constant voltage of 140 V for 30 minutes. In addition, for a molecular weight standard, electrophoresis of three kinds of sodium polyphosphate having an average degree of polymerization of 14, 60 or 130 was carried out together with a specimen of each fraction.

After the electrophoresis, each of the polyphosphoric acids was visualized by coloring the gel with toluidine blue. The image of the colored gel was scanned by means of an image scanner [GT-8300UF, manufactured by SEIKO EPSON CORPORATION], and retrieved as a necessary data. The mobility (migration distance) was analyzed with the above-mentioned image analysis program Image J. The analysis was carried out by determining the coordinate of the tip point and the end point of mobility in each specimen by the number of pixels, and the middle point between the tip point (lower molecular weight side) and the end point (higher molecular weight side) was calculated by the number of pixels. The value of the pixels from the tip point to the middle point was calculated, and regarded as a point corresponding to average degree of polymerization. The mobility of some molecular weight standards is shown in Table 5.

TABLE 5

| Average Degree of Polymerization (n) | log(n) | Mobility (pixel) |
|---|---|---|
| 14 | 1.15 | 551.5 |
| 60 | 1.78 | 364.5 |
| 130 | 2.11 | 214.0 |

From the results shown in Table 5 and logarithm [y: log(n)] of the average degree of polymerization to the mobility (x), a calibration curve represented by the equation:

$$y=-0.002888x+2.767214$$

wherein squared correlation coefficient (R2) is 0.987385, was obtained.

Also, from the results of the above-mentioned calibration curve and the mobility of each specimen, the average degree of polymerization of each speci men was calculated. The results are shown in Table 6.

TABLE 6

|  |  | Mobility (pixel) | log (n) | Average Degree of Polymerization (n) |
|---|---|---|---|---|
| Example 15 | Sodium ultraphosphate | 524.0 | 1.254 | 17.9 |
| Example 16 | Fraction A | 562.5 | 0.883 | 18.2 |
| Example 17 | Fraction B | 633.5 | 0.938 | 11.8 |
| Example 18 | Fraction C | 609.5 | 1.007 | 11.3 |
| Example 19 | Fraction D | 594.0 | 1.052 | 10.2 |
| Example 20 | Fraction E | 587.5 | 1.071 | 8.7 |
| Example 21 | Fraction F | 522.0 | 1.260 | 7.6 |

As shown in Table 6, the average degree of polymerization of fractions C to E, which were more excellent in removal effect of stain and plaque than that of a salt of ultraphosphoric acid before fractionating, was 8.7 to 11.3, and the average degree of polymerization of fraction D, which was most excellent in removal effect of stain and plaque of all, was 10.2.

From the results shown in Table 6, according to fraction F having a low average degree of polymerization and fractions A and B having a high average degree of polymerization, it was observed that the removal activity of stain and plaque of those fractions was almost equal to or lower than that of the salt of ultraphosphoric acid before fractionating. From this fact, it can be seen that it is appropriate for the salt of ultraphosphoric acid to have an average degree of polymerization in a specific range.

Example 22 and Comparative Example 3

Stain Deposition Controlling Test

As test solutions, 100 mM (concentration of phosphoric acid) of sodium ultraphosphate aqueous solution (pH 6.2) and 100 mM (concentration of phosphoric acid) of sodium metaphosphate aqueous solution (pH 6.2) were prepared respectively in the same manner as in Example 1.

Next, 150 mg of hydroxyapatite powder was put into a 15 mL centrifuge tube, 10 mL of purified water or 10 mL of each test solution was added thereto, and the centrifugal tube was tipped over to mix them. This mixed solution was centrifuged (1,500 g, 2 minutes) by means of a centrifugal separator [5200 type, manufactured by Kubota Corporation], to remove a supernatant. Purified water in an amount of 10 mL was added to the residue, and the centrifugal tube was tipped over to mix them for 1 minute. Thereafter, the mixed solution was centrifuged again (1,500 g, 2 minutes) to remove a supernatant, and the resulting hydroxyapatite powder was washed. After repeating this operation again, 5 mL of the tea extract was added to the hydroxyapatite powder, and the centrifugal tube was tipped over to mix them for 1 minute.

Thereafter, the mixture of this hydroxyapatite powder and the tea extract was centrifuged (1,500 g, 2 minutes) by means of a centrifugal separator, the supernatant was removed, and 10 mL of purified water was added to the mixture. The mixture was tipped over and mixed for 1 minute, and centrifuged (1,500 g, 2 minutes). After removing the supernatant from the above-mentioned mixed solution, 13 mL of purified water was added to the mixed solution, and the mixed solution was tipped over to mix them for 1 minute. The mixed solution was filtered through a filter pad [Cat. No. AP10, manufactured by Millipore Corp., Japan] by suction filtration.

Next, deposition ratio of the tea stain was calculated by using this filter pad in the same manner as in Example 1. With respect to the deposition ratio of the tea stain in each test solution, the deposition ratio was regarded as 100% when treated with purified water instead of the test solution in the same manner as mentioned above, and the deposition ratio was regarded as background (deposition ratio:0%) when treated with only purified water without the addition of the tea extract in the same manner as mentioned above. The results are shown in Table 7.

TABLE 7

|  |  | Deposition ratio of stain (%) |
|---|---|---|
| Example 22 | Sodium ultraphosphate | 1.33 |
| Comparative Example 3 | Sodium metaphosphate | 2.29 |

From the results shown in Table 7, it can be seen that the effect for preventing the tooth surface from the deposition of stain exhibited by the salt of ultraphosphoric acid was about 1.7 times higher than that exhibited by the salt of metaphosphoric acid.

Hereinafter, Prescription Examples of the oral composition according to the present invention are described. The content of each component is represented by % by weight.

Prescription Example 1

Powder Type Mouth Rinse

| Silicic anhydride | 2.5 |
|---|---|
| Sodium ultraphosphate (fraction D obtained in Example 19) | 3.0 |
| Sodium saccharine | 0.2 |
| Coloring agent | proper amount |
| Perfume | proper amount |
| Sodium hydrogen carbonate | remainder |
| Total | 100 |

Prescription Example 2

Mouth Rinse

| Ethanol | 1.0 |
|---|---|
| Glycerin | 2.5 |
| Polyoxyethylene hydrogenated castor oil | 1.0 |
| Sodium ultraphosphate (fraction D obtained in Example 19) | 4.5 |
| Sodium saccharine | 0.15 |
| Sodium benzoate | 0.05 |
| Sodium dihydrogen phosphate | 3.5 |
| Coloring agent | proper amount |
| Perfume | proper amount |
| Purified water | remainder |
| Total | 100 |

Prescription Example 3

Tooth Powder

| Sodium lauryl sulfate | 2.0 |
|---|---|
| Sodium ultraphosphate (fraction D obtained in Example 19) | 4.0 |
| Sodium saccharine | 0.1 |
| Purified water | proper amount |
| Perfume | proper amount |
| Calcium carbonate | remainder |
| Total | 100 |

Prescription Example 4

Liquid Dentifrice

| Ethanol | 10.5 |
|---|---|
| Glycerin | 4.5 |
| Sodium lauryl sulfate | 1.2 |
| Sodium ultraphosphate (fraction D obtained in Example 19) | 5.0 |
| Polyoxyethylene polyoxypropylene glycol | 0.5 |
| Sodium saccharine | 0.15 |
| Sodium benzoate | 0.1 |
| Perfume | proper amount |
| Coloring agent | proper amount |
| Purified water | remainder |
| Total | 100 |

Prescription Example 5

Toothpaste

| Dibasic calcium phosphate dihydrate | 45.0 |
|---|---|
| Silicic anhydride | 2.0 |
| Glycerin | 15.0 |
| Carboxymethylcellulose sodium | 0.8 |
| Carrageenan | 0.3 |
| Sodium lauryl sulfate | 1.5 |
| Sodium ultraphosphate (fraction D obtained in Example 19) | 4.0 |

| | |
|---|---|
| Saccharine sodium | 0.15 |
| Hinokitiol | proper amount |
| Perfume | proper amount |
| Paraben | proper amount |
| Purified water | remainder |
| Total | 100 |

INDUSTRIAL APPLICABILITY

Since the oral stain remover and the oral composition of the present invention prevent stain from being deposited on the surface of teeth, and moreover exhibit excellent removal effect of stain or plaque, the oral stain remover and the oral composition can be suitably used in oral preparations such as dentifrice, mouth rinse, denture cleaner and tooth patch.

The invention claimed is:

1. An oral composition comprising an oral stain remover comprising a salt of ultraphosphoric acid represented by the formula:

$$\frac{x}{2}M_2O \cdot \frac{y}{2}P_2O_5 \qquad (III)$$

wherein M is an alkali metal, and each of x and y is a positive integer and satisfies 0<x/y<1;
wherein the average degree of polymerization of the salt of ultraphosphoric acid is 8.5 to 11.5; and
wherein the content of the salt of ultraphosphoric acid is 0.5 to 10% by weight.

2. The oral composition according to claim 1, wherein pH of the oral composition is 4 to 8.

* * * * *